(12) United States Patent
Rosenblum et al.

(10) Patent No.: US 6,214,974 B1
(45) Date of Patent: Apr. 10, 2001

(54) AVIDIN-BIOTIN IMMUNOCONJUGATES

(75) Inventors: Michael G. Rosenblum, Sugar Land; Nicholas J. Donato, Houston, both of TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 08/410,390

(22) Filed: Mar. 27, 1995

Related U.S. Application Data

(63) Continuation of application No. 08/192,655, filed on Feb. 7, 1994, now abandoned.

(51) Int. Cl.⁷ .................. A61K 39/395; C07K 16/28
(52) U.S. Cl. ................ 530/391.9; 424/172.1; 424/173.1; 424/174.1; 424/179.1; 424/181.1; 424/183.1; 530/367; 530/388.2; 530/388.22; 530/388.7; 530/388.8; 530/389.6; 530/389.7; 548/303.7
(58) Field of Search ............... 424/183.1, 178.1, 424/172.1, 173.1, 174.1, 179.1, 181.1; 530/388.22, 388.8, 389.7, 391.5, 391.7, 367, 388.2, 388.7, 389.6, 391.9; 548/303.7

(56) References Cited

U.S. PATENT DOCUMENTS 4,545,985 * 10/1985 Pastan ............................... 424/183.1

FOREIGN PATENT DOCUMENTS

0251494 * 1/1988 (EP) .

OTHER PUBLICATIONS

Vitetta et al., Tips, 1993, 14:148.*
Wilchek et al., Anal. Biochem., 1988, 171:1.*
Osband, Immunol. Today, 1990, 11:193.*
Chatterjee, Cancer Immunol. Immunother., 1994, 38:78.*
Zwierzina, Stem Cells, 1993, 11:144.*
Curti, Crit. Rev. Oncol. Hemalol., 1993, 14:29.*
Jain, Scientific Am., 1994, 271:58.*
Martinez, Cancer Surveys, 1(3):374, 1982.*
Pastan, Cell, 47: 641, 1986.*
Chen et. al, FEBS Letters, 338:167–169 (1994).

* cited by examiner

*Primary Examiner*—David Saunders
(74) *Attorney, Agent, or Firm*—Benjamin Aaron Adler

(57) ABSTRACT

The present invention provides a non-viral vector, comprising a cell binding component having a biotin-binding element conjugated to a biotinylated moiety. Also, provided is a method of introducing genetic material inside a specific cell comprising the administration of the non-viral vector to a human, wherein said non-viral vector comprises a cell binding component having a biotin-binding element conjugated to a biotinylated moiety. In addition, there is provided a method of delivering a cytotoxic moiety to a cell comprising the administration of the non-viral vector to a human.

8 Claims, 11 Drawing Sheets

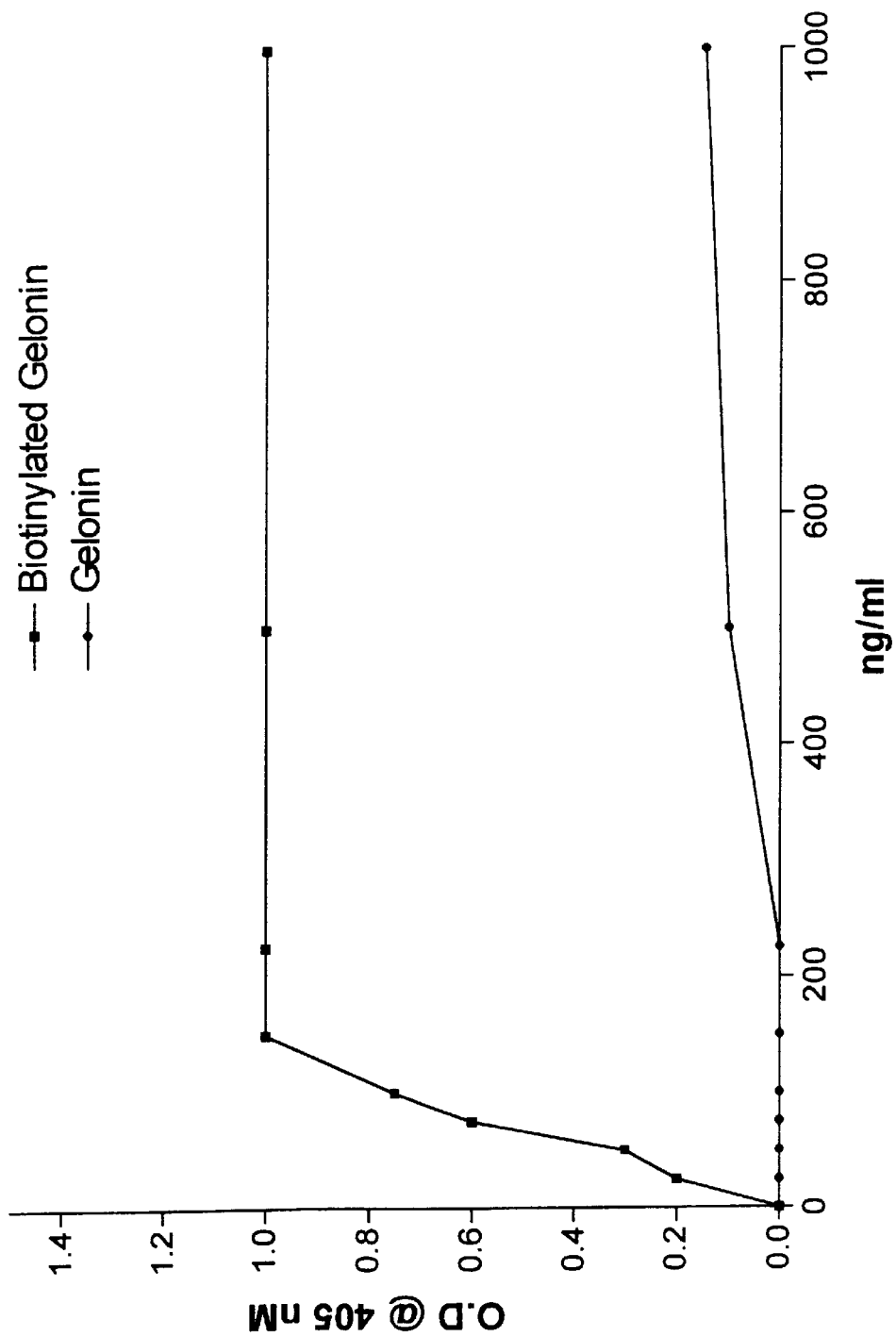

SEQUENCE LISTING

```
<160> NUMBER OF SEQ ID NOS:  3

<210> SEQ ID NO 1
<211> LENGTH: 15
<212> TYPE: DNA
<213> ORGANISM: artificial sequence
<220> FEATURE:
<223> OTHER INFORMATION: Antisense nucleic acid sequence against c-myc

<400> SEQUENCE: 1
aacgttgagg ggcat                                                    15

<210> SEQ ID NO 2
<211> LENGTH: 15
<212> TYPE: DNA
<213> ORGANISM: artificial sequence
<220> FEATURE:
<223> OTHER INFORMATION: Antisense nucleic acid sequence against
      translation start site in bFGF mRNA

<400> SEQUENCE: 2
ggctgccatg gtccc                                                    15

<210> SEQ ID NO 3
<211> LENGTH: 15
<212> TYPE: DNA
<213> ORGANISM: artificial sequence
<220> FEATURE:
<223> OTHER INFORMATION: Antisense oligonucleotide sequence against
      5' flanking sequence in c-HA-ras mRNA

<400> SEQUENCE: 3
cagctgcaac ccagc                                                    15
```

AVIDIN-BIOTIN IMMUNOCONJUGATES

This is a continuation of application Ser. No. 08/192,655 filed on Feb. 7, 1994, now abandoned.

BACKGROUND OF THE INVENTION

1. Field of the Invention

The present invention relates generally to the field of molecular biology and therapeutics. More specifically, the present invention relates to a novel non-viral vector for the delivery of genetic information to cells.

2. Description of the Related Art

Currently, the most common mechanism for delivery of genetic material capable of affecting molecular properties of mammalian cells utilizes viral, primarily retroviral, vectors. However, this mode of genetic therapy or delivery is influenced by several deficiencies and potentially hazardous conditions. Although retroviral vectors have been more common, adenoviral vectors are now being studied and both have some potential. Unfortunately, a viral vector has many disadvantages. First, the target cells, e.g., human cells, must be capable of interacting with viruses through expression of a specific cell surface element which may not be expressed on the cells or tissue of interest for delivery of genetic information. Second, the genetic material must be integrated and expressed in the target, e.g., human cell, which requires that target cells be actively dividing, a condition hindering the efficiency and homogeneity of this delivery system. Even if successfully integrated, the gene may be transcriptionally silent by host cell mechanisms. Third, the size of the genetic information allowable in this system is limited and must be engineered with great precision to ensure biologic activity. Fourth, the replication defective viruses must be utilized for gene therapy applications to reduce the risk of recombination with endogenous viruses which may form new infectious agents. Replication defective viruses may reduce this hazard but do not eliminate it. Fifth, the replication defective viruses are by design not self-removing, requiring repetitive infection to achieve successful delivery of gene sequences to all cells.

The prior art is deficient in the absence of non-viral vectors. The present invention fulfills this longstanding need and desire in the art.

SUMMARY OF THE INVENTION

The present invention provides, inter alia, a novel non-viral system for delivery of genetic materials capable of modification of deleterious or undesirable phenotypic characteristics.

Thus, in one embodiment of the present invention there is provided a non-viral vector, comprising a cell binding component having a biotin-binding element conjugated to a biotinylated moiety.

In another embodiment of the present invention, there is provided a method of introducing genetic material inside a specific cell comprising the administration of the non-viral vector to a human, wherein said non-viral vector comprises a cell binding component having a biotin-binding element conjugated to a biotinylated moiety.

In yet another embodiment of the present invention, there is provided a method of delivering a cytotoxic moiety to a cell comprising the administration of the non-viral vector to a human.

Other and further aspects, features, and advantages of the present invention will be apparent from the following description of the presently preferred embodiments of the invention given for the purpose of disclosure.

BRIEF DESCRIPTION OF THE DRAWINGS

The following figures are provided to illustrate various aspects of the present invention. To that end, some of the figures are presented in schematic form and are not necessarily drawn to scale.

FIGS. 6A and 6B show the binding activity for assay of biotinylated gelonin.

DETAILED DESCRIPTION OF THE INVENTION

Figure 1:
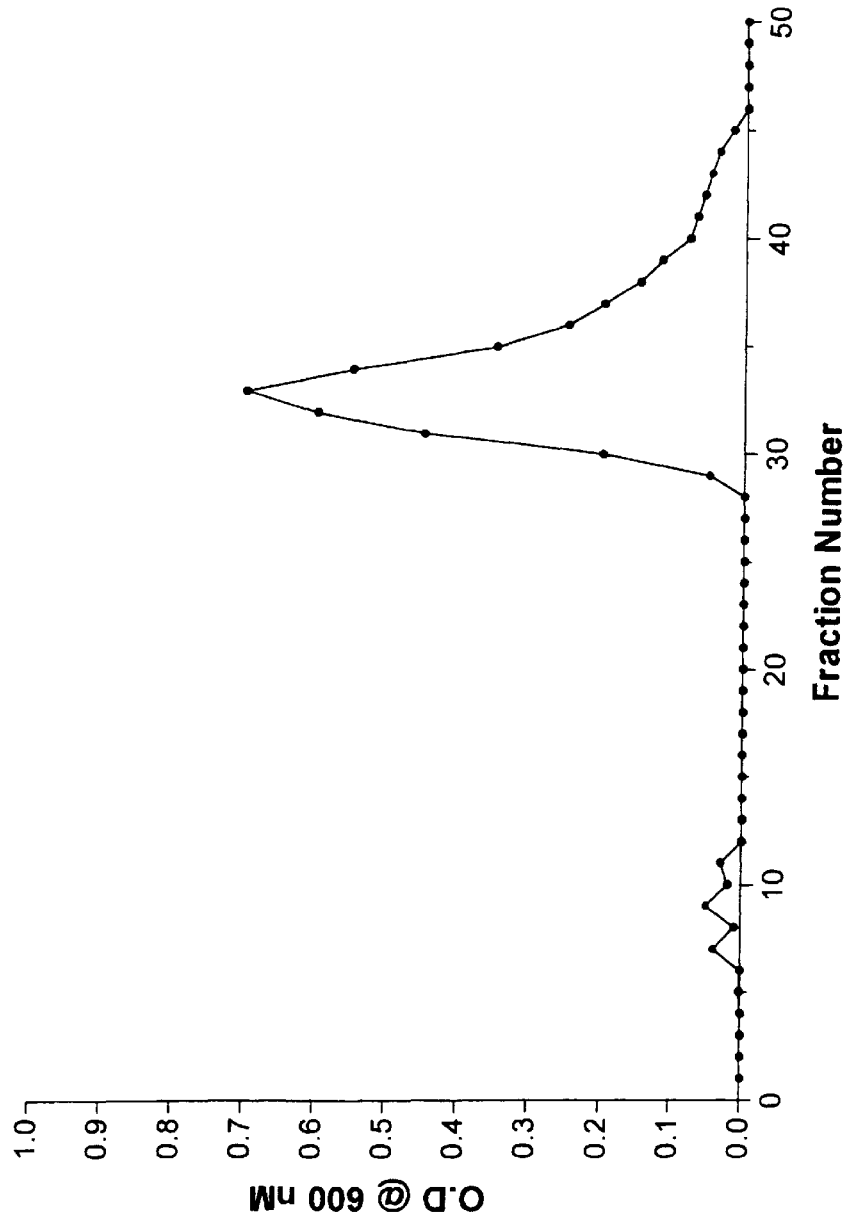
FIG. 1 shows the separation of free SPDP from A108/SPDP on G-25 column.

The present invention provides a non-viral vector, comprising a cell binding component having a biotin-binding element conjugated to a biotinylated moiety.

Generally, the biotin-binding element of the present invention is any that chemical that binds biotin and would be easily recognizable by a person having ordinary skill in this art. Preferably, the biotin-binding element is selected from the group consisting of avidin, streptavidin or analogues of avidin or streptavidin.

The cell binding element of the present invention may be one of several different embodiments. For example, the cell binding element may be a monoclonal antibody. Monoclonal antibody useful in the compositions and methods of the present invention are those that specifically bind an antigen. Representative examples of antigens to which such antibodies would bind are epidermal growth factor receptor, c-erbB2 antigen, Lewis Y antigen, transferrin receptor, MDR1, MDR3, insulin receptor, CD45, CD33, GP240, GD2, GD3, fibroblast growth factor receptor, platelet derived growth factor receptor.

Alternatively, the cell binding element is a ligand which specifically binds a cell surface receptor. Representative examples of ligands binding cell surface receptors include transforming growth factor-alpha, heregulin, fibroblast growth factor, platelet-derived growth factor receptor.

Generally, the biotinylated moiety may be any compound which can be appropriately biotinylated and which is a chemical which one desires to specifically introduce inside a cell to exert a particular biological or pharmacological effect. Thus, the biotinylated moiety may be a protein or a nucleic acid.

Representative examples of proteins useful in the compositions and methods of the present invention are gelonin, ricin, saporin, abrin, diptheria toxin, psuedomonas exotoxin, rayalase, superoxide dismutase, protein tyrosine phosphatase, protein phosphatase (PP-1 or PP-2), protein kinase A and protein kinase C.

Representative examples of nucleic acids are triple helix oligonucleotides, e.g., triplex EGF receptor oligonucleotides, anti-sense oligonucleotides, e.g., for EGF or myc, partial gene sequences, e.g., sequences encoding a single domain of a protein with several domains such as c-src or the EGF receptor and entire genes, i.e., taken from an integrative unit of the retroviral genome.

The present invention also provides a method of introducing genetic material inside a specific cell comprising the administration of the non-viral vector to a human, wherein said non-viral vector comprises a cell binding component having a biotin-binding element conjugated to a biotinylated moiety.

The present invention also provides a method of delivering a cytotoxic moiety to a cell comprising the administration of the non-viral vector to a human.

The present invention involves compositions and methods permitting the introduction of nucleic acids into a specific subset of cells without using a viral infection or transfection component. Monoclonal antibodies directed against a cell-surface component are modified and utilized to carry, to the intracellular compartment, nucleic acids capable of modifying gene expression, specifically increasing or decreasing the level of protein expressed within target cells. The present invention is applicable for anti-sense nucleic acid technology in humans.

Monoclonal antibodies directed against a cell surface component are modified with a biotin-binding moiety and nucleic acid sequences that bind genomic DNA or mRNA sequences such that gene expression is altered and are linked through avidin:biotin interaction using biotinylated derivatives of nucleic acid sequences. Through internalization of antibody:antigen complexes, active nucleic acid sequences are cointernalized, increasing the intracellular content of these sequences. Use of the present invention: (1) increases intracellular content of gene expression modulating nucleic acid sequences by mechanisms other than those related to viral vectors or through simple or facilitated diffusion through the plasma membrane; (2) allows one to bypass the restrictions of small molecular size, i.e., of active nucleic acid sequences (-20-mers) by eliminating the need of simple diffusion through the plasma membrane as the mechanism of entry of these sequences into the cell; and (3) delivers sequences of interest to cells specifically or selectively through an antibody:antigen interaction rather than through global delivery or viral infection to increase cellular content of active nucleic acid sequences.

In one embodiment of the present invention, one synthesizes anti-sense DNA against an oncogenic protein which spans nucleotides (10) upstream and downstream of the mRNA translation start codon. Then, one synthesizes DNA complimentary to the first 5 nucleotides of the anti-sense DNA synthesized above. Then, one incorporates into that sequence a biotin-nucleotide moiety. The two strands are hybridized. Then, deliver via tumor targeting the MAb Avidin/Streptavidin to tumor.

The following examples are provided for the sole purpose of illustrating various embodiments of the present invention and are not meant to limit the present invention in any fashion.

EXAMPLE 1
Modification of Antibody A108

A108 recognizes the human receptor for epidermal growth factor. 10 mg of A108 in 2.2 mls of phosphate-buffered saline was added to a 12×75 mm glass tube. An aliquot of 9.35 $\mu$ls of antibody and a 2.5 fold molar excess of SPDP (N-succinimidyl 3-(2-pyridyldithio)propionate) from a stock of 3 mg/ml in dimethyl formamide was added slowly to the tube while vortexing. The mixture was vortexed every five minutes during a 30 minute incubation at room temperature.

Excess unreacted SPDP was removed from the sample by gel filtration chromatography on a column (1.5×37 cm) of Sephadex G- 25 pre-equilibrated in 100 mm sodium phosphate buffer (pH 7.0) containing 0.5 mm EDTA. One ml fractions were collected on a Gilson fraction collector during buffer elution. Fractions were analyzed for protein content in a 96-well microtiter plate (Falcon) using the Bradford dye binding assay. Each well contained 120 $\mu$l of PBS, 40 $\mu$l of dye concentrate and 40 $\mu$l of sample. Absorbance was read on a BioTek Microplate Autoreader at 540 nm. Fractions 30–38 were pooled and kept at 4° C.

FIG. 1 shows the addition of SPDP to anti-EGFr antibody (A108) through covalent coupling. A108 was modified through lysine and N-terminal amino acid modification using SPDP. The unreacted material was removed from the high molecular weight A108 by gel filtration. The elution profile of SPDP-modified A108 is shown in FIG. 1. FIG. 1 demonstrates that modified A108 was recovered after SPDP conjugation.

Figure 2:
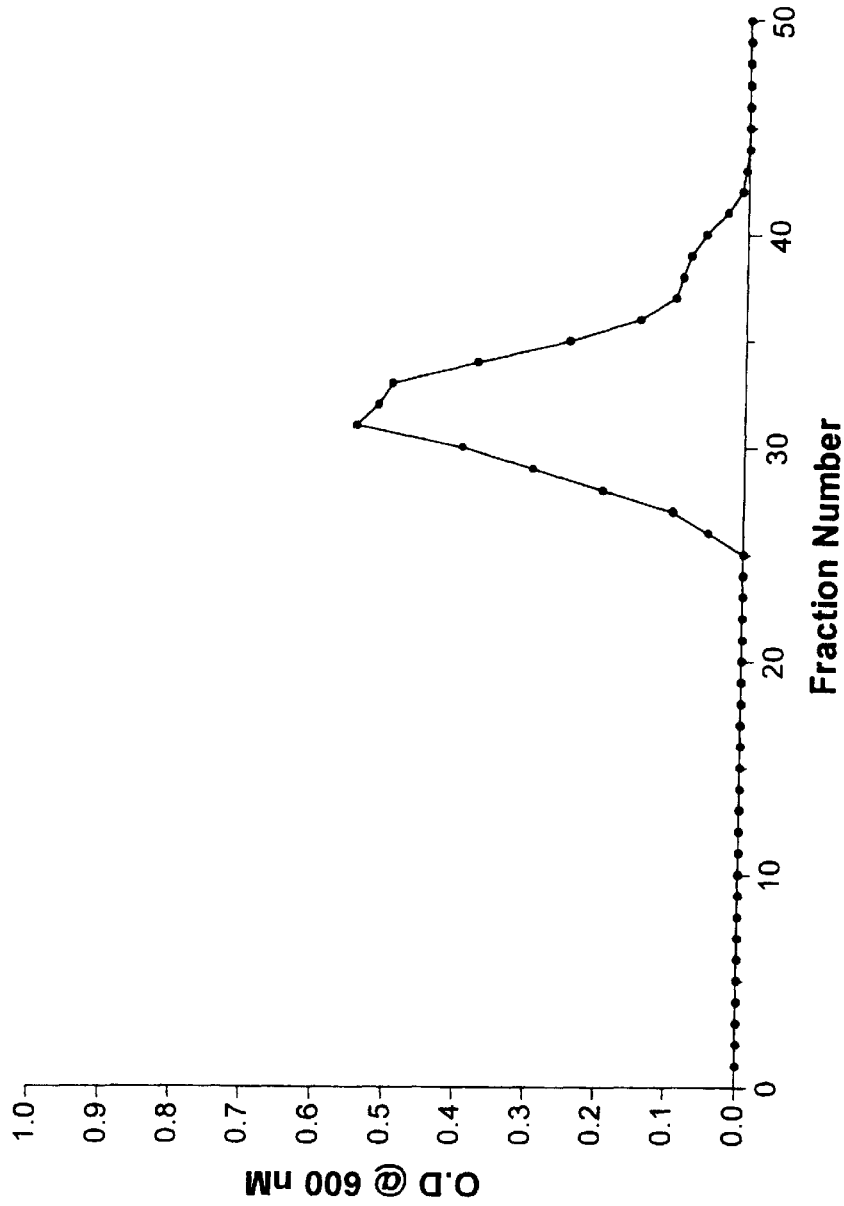
FIG. 2 shows the separation of free 2-IT from avidin/2-IT on G-25 column.

EXAMPLE 2
Modification of Avidin—Egg White 10 mg of avidin in 2.5 ml double distilled water (ddH$_2$O) was diluted to contain 60 mM TEA/HCl (tri-ethanolamine, pH 8.0) and 1 mM EDTA by addition of 300 ul 0.5 mM TEA/HCl and 28 $\mu$l 0.1 mM EDTA stock solutions. The final volume was 2.8 ml. Seventeen uls of 2-imino-thiolane (2-IT) TEA/HCl (pH 8.0) was then added for a final concentration of 3 mM. The sample was incubated for 90 minutes at 4° C. under a stream of nitrogen gas. Excess unreacted 2-IT was removed by gel filtration chromatography using a G-25 Sephadex column (1.5×38 cm) (Pharmacia) pre-equilibrated with 5 mM bis-tris/acetate buffer (pH 5.8) containing 50 mM NaCl and 1 mM EDTA. The protein content of the eluted fractions was determined by the Bradford dye binding assay. Absorbance was read on a BioTek Microplate Autoreader at 540 nm. Fractions (1 ml each) 27–38 were pooled. Avidin modified with 2-iminothiolane was recovered by gel filtration as shown in FIG. 2.

EXAMPLE 3
Conjugation of antibody A108 and avidin

The modified antibody and modified avidin fractions were incubated together at 4° C. under a stream of nitrogen gas for 20 hours (15.5 ml total volume). A solution of 0.1M iodoacetamide (0.310 ml) was added to make a final concentration of 2 mM to block any remaining free sulfhydryl groups, and incubation continued for 1 hour at room temperature. SPDP-modified A108 and 2-iminothiolane-modified avidin were incubated together so that A108 would become covalently bound to the avidin through a sulphydryl linkage supplied by SPDP: 2-iminothiolane chemistry.

The immunoconjugate composed of A108-avidin (labeled as conjugate in FIG. 3) was separated from unreacted avidin by gel filtration. The peak of protein eluting into fractions 7–9 represents unmodified A108 and A108-avidin which was recovered and further purified.

EXAMPLE 4
Purification of Conjugate

Figure 3:
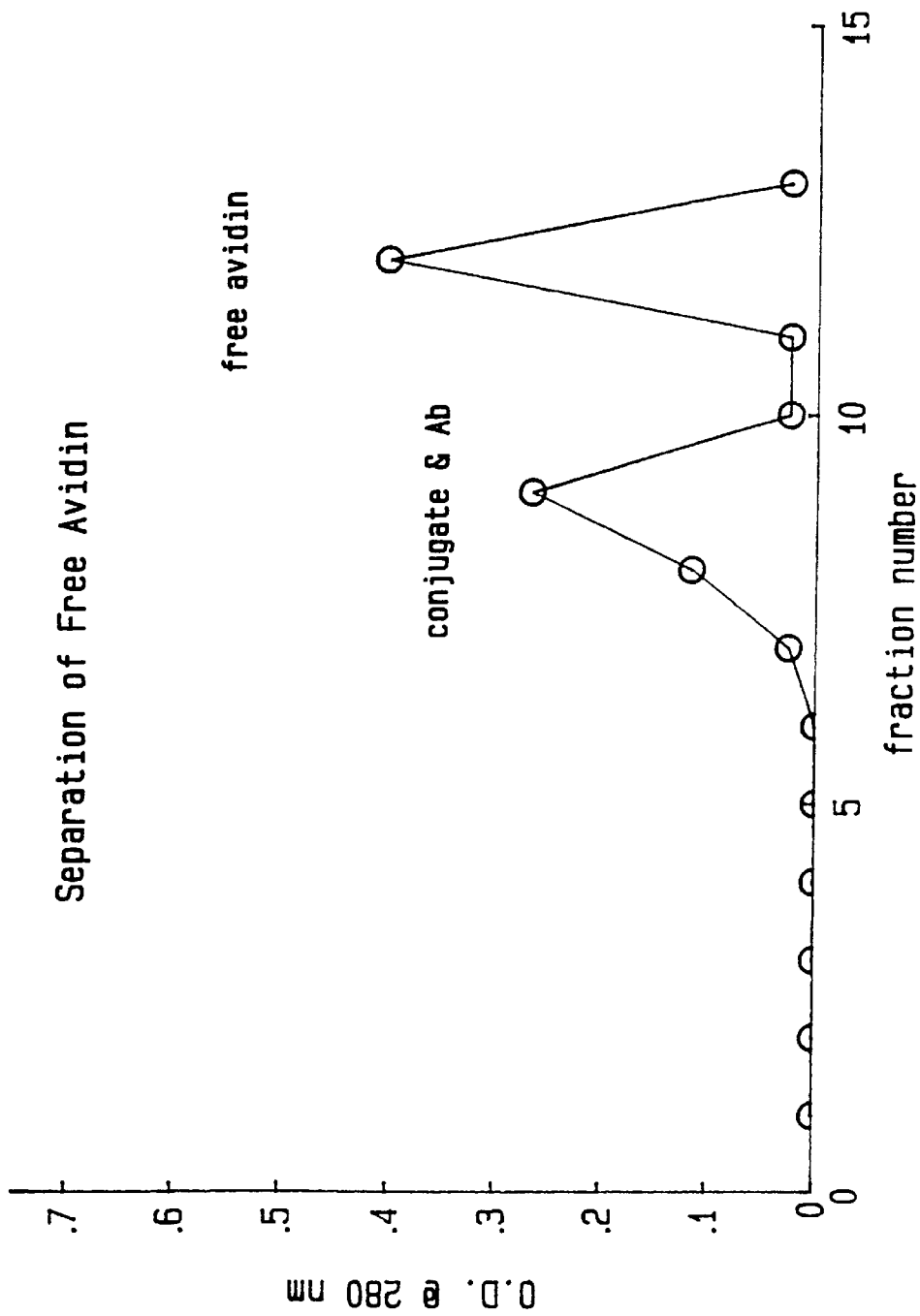
FIG. 3 shows the separation of free avidin from A108-avidin conjugate on S-200 column (FPLC).

Non-conjugated avidin was removed from the reaction mixture by gel filtration on a Pharmacia FPLC Superdex S-200 column (2.6×60 cm) pre-equilibrated with 20 mM Tris and 150 mM NaCl (pH 7.4). [FIG. 3]

The antibody-avidin conjugate and free antibody fractions (6–10) were pooled and dialyzed (Spectra/Par molecular porous membrane tubing #2 MWCO 12,000–14,000) overnight against PBS at 4° C. The free antibody was removed from the mixture by use of a concavalin-A (Vector) agarose bound affinity. Column (1.5 cm×7 cm) pre-equilibrated PBS (20 MM Na-K-phosphate, 150 mM NaCl, pH 7.0). After sample loading, the column was washed once with 40 ml of PBS containing 1M NaCl (pH 7.0), and the conjugate was eluted with PBS containing 200 mM of methyl-D-mannose (pH 7.0) (fractions 34–38) (2 mls each). The protein content of the eluted fractions was measured on a Varian Spectrophotometer at 280 mm.

Through binding of the carbohydrate moiety on avidin, A108-avidin was separated from A108 by its retention on an immobilized support of the plant lectin concanavalin A (Con A) which binds alpha-methylmannoside (which is present on avidin).

Figure 4:
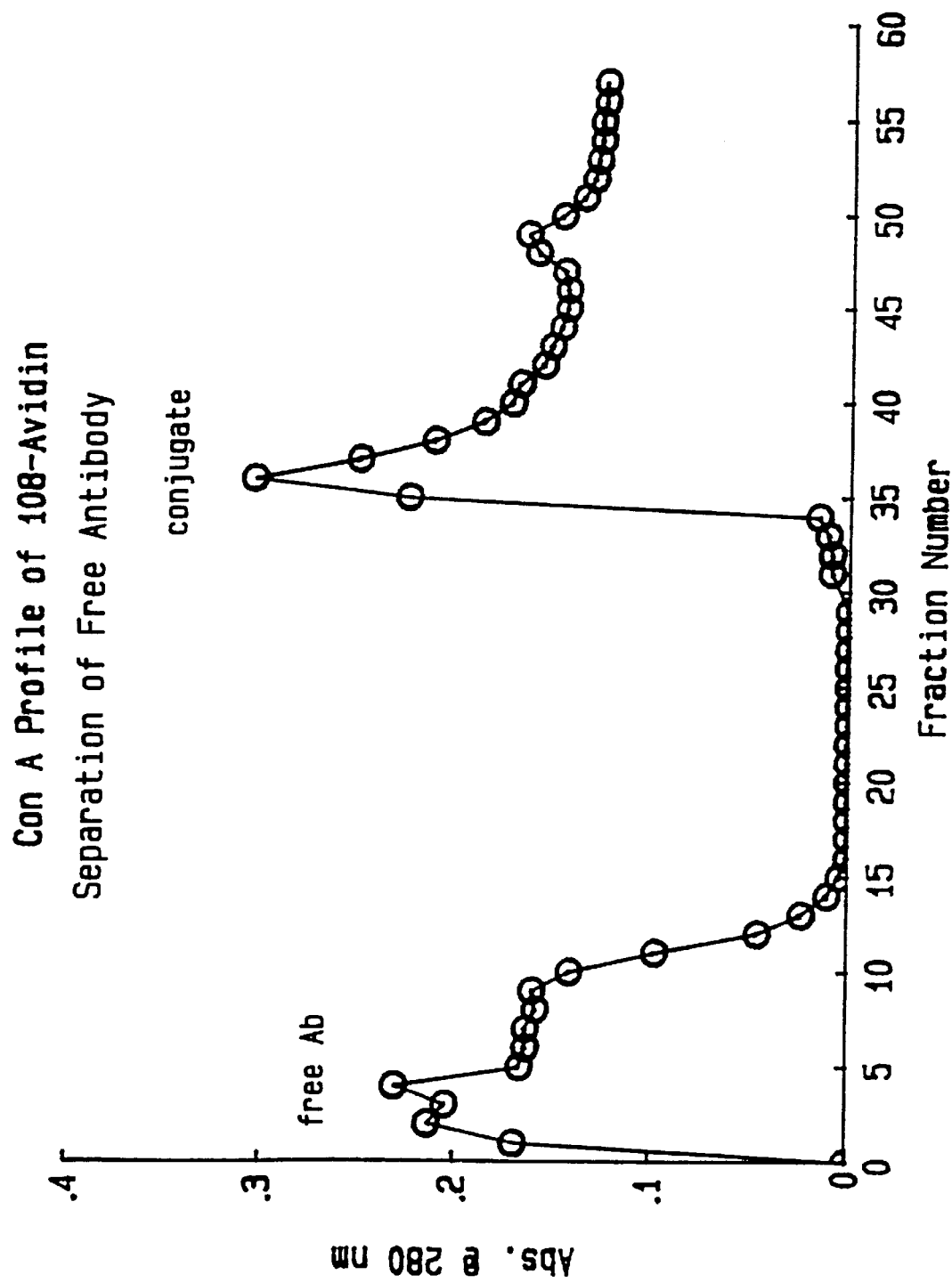
FIG. 4 shows the separation of free antibody from A108-avidin conjugate on Con-A column.

Free antibody has no alpha-methylmannoside and was washed through the Con A column (shown as free Ab on FIG. 4). A108-avidin (labeled as conjugate) was displaced from the Con A-Sepharose column using elution with alpha-methylmannoside in solution. The conjugate was recovered by this procedure and was free of unmodified A108.

Figure 5:
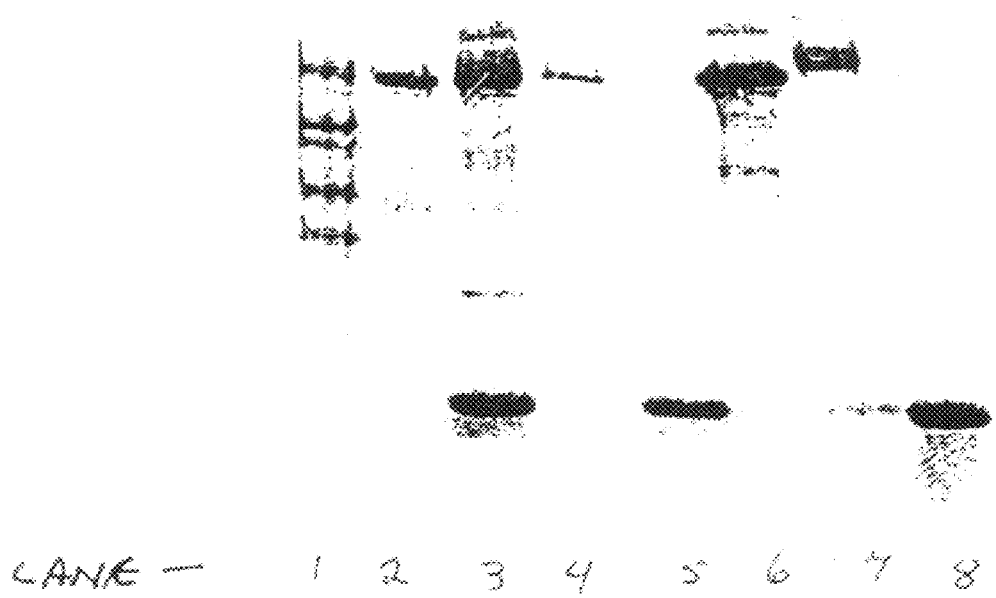
FIG. 5 shows a 7.5% SDS-PAGE mini-gel showing purification steps of A108-avidin conjugate.

The purity of the A108-avidin conjugate was monitored by sodium dodecyl sulfate polyacrylamide gel electrophoresis (SDS-PAGE) which separates proteins based upon their molecular size. A 7.5% acrylamide SDS-PAGE mini gel was run to examine the purification steps of the conjugation. As shown in FIG. 5, proteins representing A108, avidin or conjugates of A108-avidin were resolved and visualized when proteins were subjected to staining with Cooomasie blue dye in the polyacrylamide gel and destained to eliminate background. The sample applied to lane 7 (eluate from the Con A column) represents the purified immunoconjugate (A108-avidin) which was utilized in subsequent studies.

The ability of A108-avidin to bind biotin and internalize into eukaryotic cells can be demonstrated utilizing a biotinylated protein having toxic activity only when internalized into cells (e.g., the plant protein, gelonin). Purified gelonin protein was chemically modified with biotin (by covalently bonding through lysine residues on gelonin with NHS-biotin) and purified from unbound biotin by gel filtration.

EXAMPLE 5
Biotinylation of gelonin

Figure 6A:
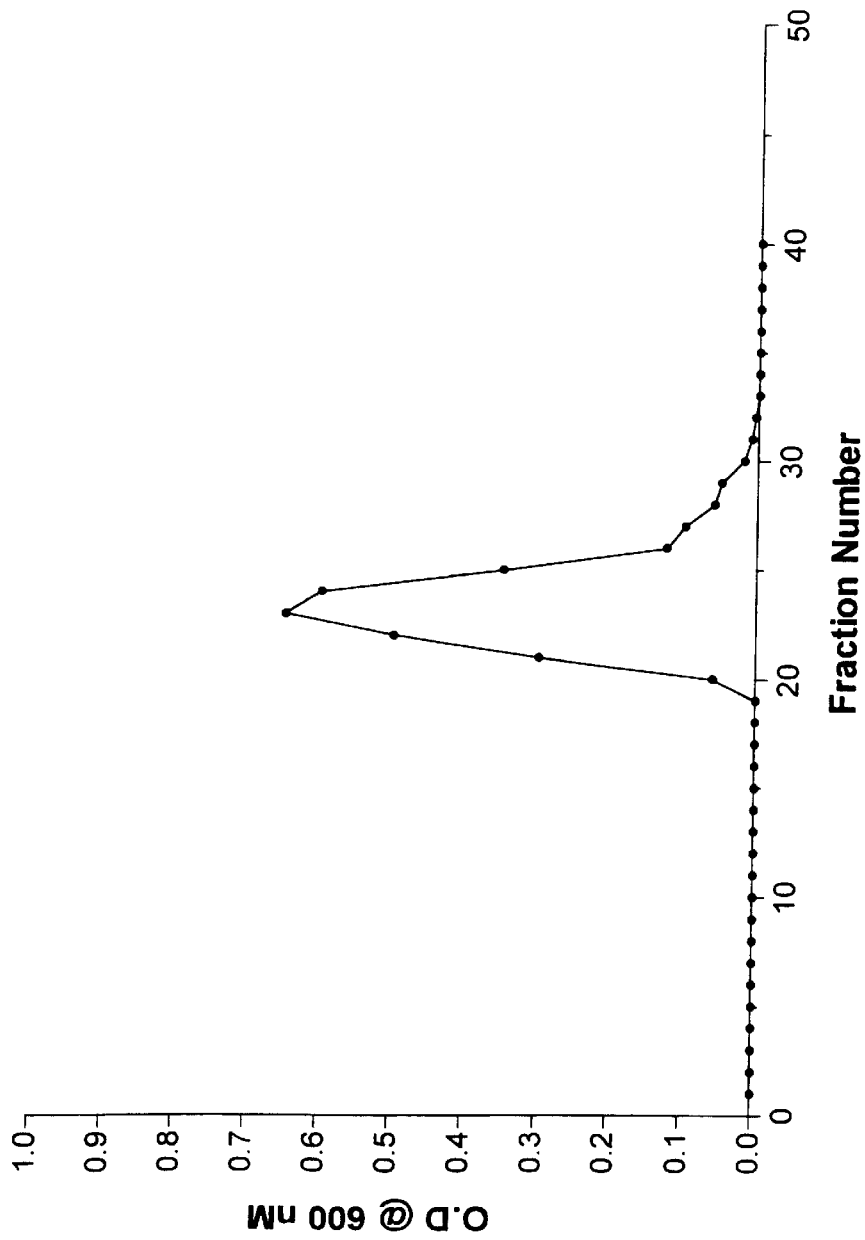

The biotin used was in the form of N-hydroxy succinimide ester long chain (NHS-LC) Biotin (Pierce Chemical Co.). A five-fold molar excess of biotin to gelonin (=0.1 mg biotin to 1 mg gelonin) was used. The gelonin stock was 2 mg gelonin in 2 ml of a 50 mM bicarbonate buffer (pH 8.5). 5 mg biotin was dissolved in 500 µl dry dimethylformamide (DMF), and immediately 20 µl (0.2 mg) of this biotin solution was added to the gelonin in a clean, dry 13×100 mm glass tube. The sample was vortexed and incubated for 2 hours on ice. After 2 hours, the free biotin was separated by gel filtration chromatography on a 1.5 cm×37 cm G-25 column equilibrated with PBS (pH 7.0). One ml fractions were collected in a Gilson fraction collector and assayed for protein content with the Bradford dye binding assay. Fractions 21–27 (FIG. 6A) were pooled.

To demonstrate that biotin was incorporated into gelonin, the biotinylated gelonin was immobilized on a polystyrene support with an antibody directed against the gelonin protein. Indicated amounts of unmodified gelonin or biotinylated gelonin were incubated in wells containing the anti-gelonin antibody. The retention of biotin with gelonin was detected by rinsing the wells and adding streptavidin, which was chemically conjugated to the enzyme horseradish peroxidase, which when incubated with a colorless peroxidase substrate (ABTS) turns green and is measurable by spectrophotometer at the wavelength of 405 nanometers. The amount of absorbance at 405 nm is directly proportional to the amount of biotin incorporated in the gelonin molecule. As shown in FIG. 6B, the gelonin subjected to biotinylation did retain biotin, based upon the increase in green color, by increasing amounts of biotinylated gelonin placed into the assay. The results demonstrate that biotin can be incorporated into the gelonin molecule and recognized by proteins with an affinity for biotin.

EXAMPLE 6
Activity of biotinylated gelonin

A stock solution of 0.583 mg/ml murine monoclonal anti-gelonin antibody (10 Ci) (10 µl) was diluted in 12 ml coating buffer (50 mm $NHCO_3$ (sodium bicarbonate, pH: 9.6) (1 µg/ml solution). Using a multi-channel pipetor, each well of a Falcon 96-well microtiter plate was coated with 50 µl (50 ng/well). The samples were covered and refrigerated overnight. Approximately 12 hours later, the samples were rinsed three times with PBS-0.05% Tween-20 and blocked for 1.5 hours at room temperature with 5% bovine serum albumin in PBS. The sample were then washed three times with PBS and 0.05% Tween-20.

A solution of gelonin in PBS was prepared in a concentration of 2 mg/ml. Next, a solution of biotinylated gelonin in PBS was prepared, also at concentration of 2 mg/ml. 100 µl of 1 mg/ml solution of BSA in PBS was added to the plate, leaving the first row empty. To the first half of this row, 200 µl/well of the stock gelonin solution was added, and to the second half of the row 200 µl/well of the biotinylated stock solution was added. Using the multi-channel pipetor, 100 µl was withdrawn from this first row and was mixed with 100 µl BSA-PBS in the second row. This procedure was repeated from left to right across the plate resulting in the serial dilution of the protein. The plate was covered and incubated for 1.5 hours at room temperature. The wells of the plate were washed three times with PBS-0.05% Tween-20. 100 µl of Avidin Peroxidase (Boehinger-Mannheim) diluted 1:6000 in 1 mg/ml BSA-PBS, was then added. Then the plate was incubated for 1.5 hours at room temperature followed by washing three times with PBS-0.05% Tween-20. Finally, 100 µl ABTS (2, $2^1$-amino-bis (3-ethyl benz Thiazoline-6-sulfonic acid)) hydrogen peroxide was added. The plate was read on a BioTek Laboratories Microplate Autoreader at 405 nm. [FIG. 6B]

EXAMPLE 7
Conjugation of biotinylated gelonin with A108-avidin

A 5 molar excess of biotinylated gelonin to A108-avidin was used. One ml (250 µg) of A108-avidin was combined with 175 ul (175 µg) of biotinylated gelonin. The sample was vortexed and incubated together for 1 hour at room temperature.

Figure 7:
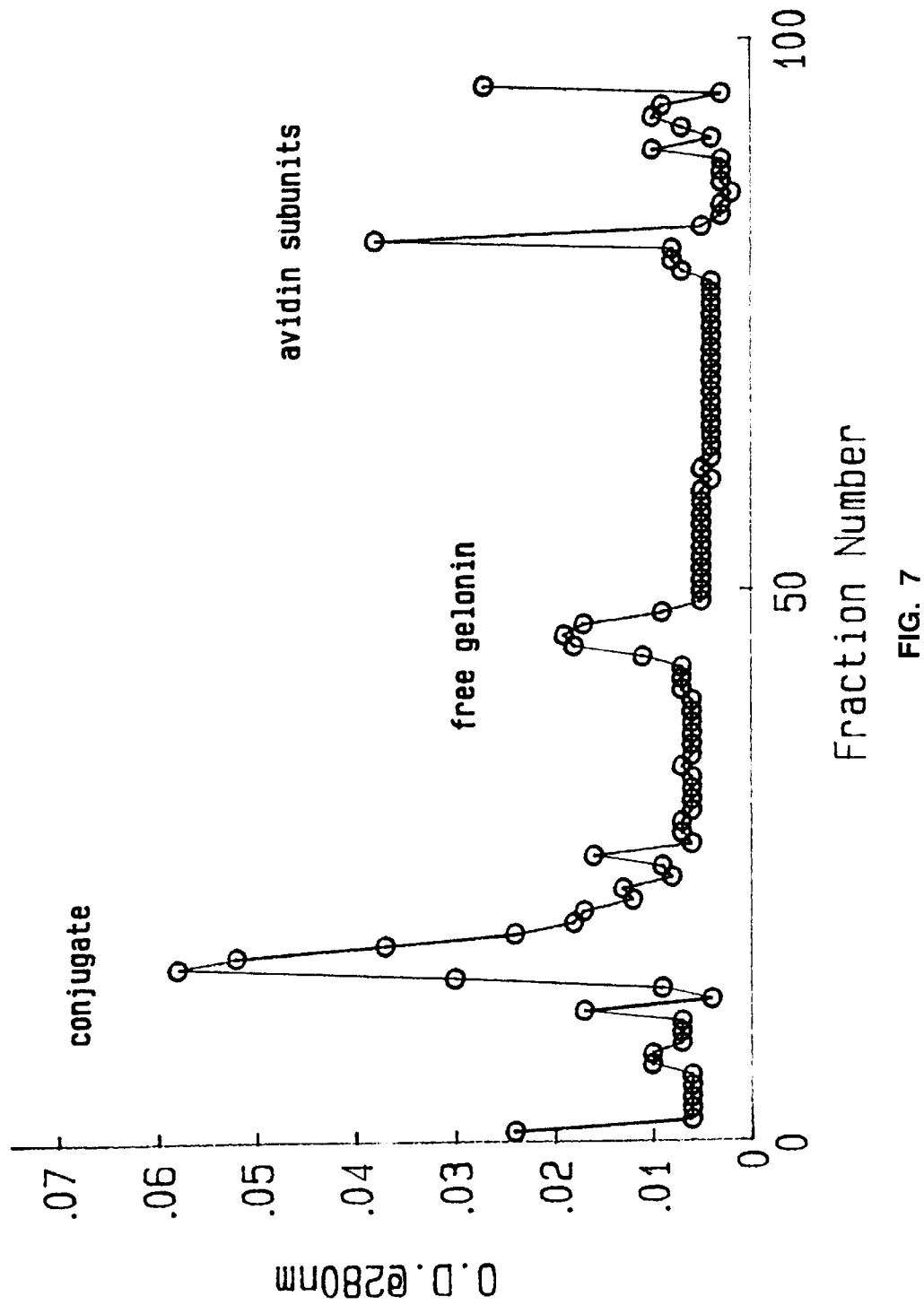
FIG. 7 shows the profile of G-75 (FPLC) for A108-avidin gelonin/biotin conjugate and the separation of free avidin gelonin and some avidin sub-units.

To remove unconjugated gelonin from the mixture, the mixture was applied to a Pharmacia FPLC G-75 (1.6×60 cm) gel filtration column pre-equilibrated with 20 mm Tris containing 0.5M NaCl (pH 7.4). One ml fractions were collected and read on a Varian Spectrophotometer at 280 nm. Peaks representing A108-avidin biotinylated gelonin labeled conjugate is shown in FIG. 7 and was free of unbound gelonin or free avidin subunits.

Figure 8:
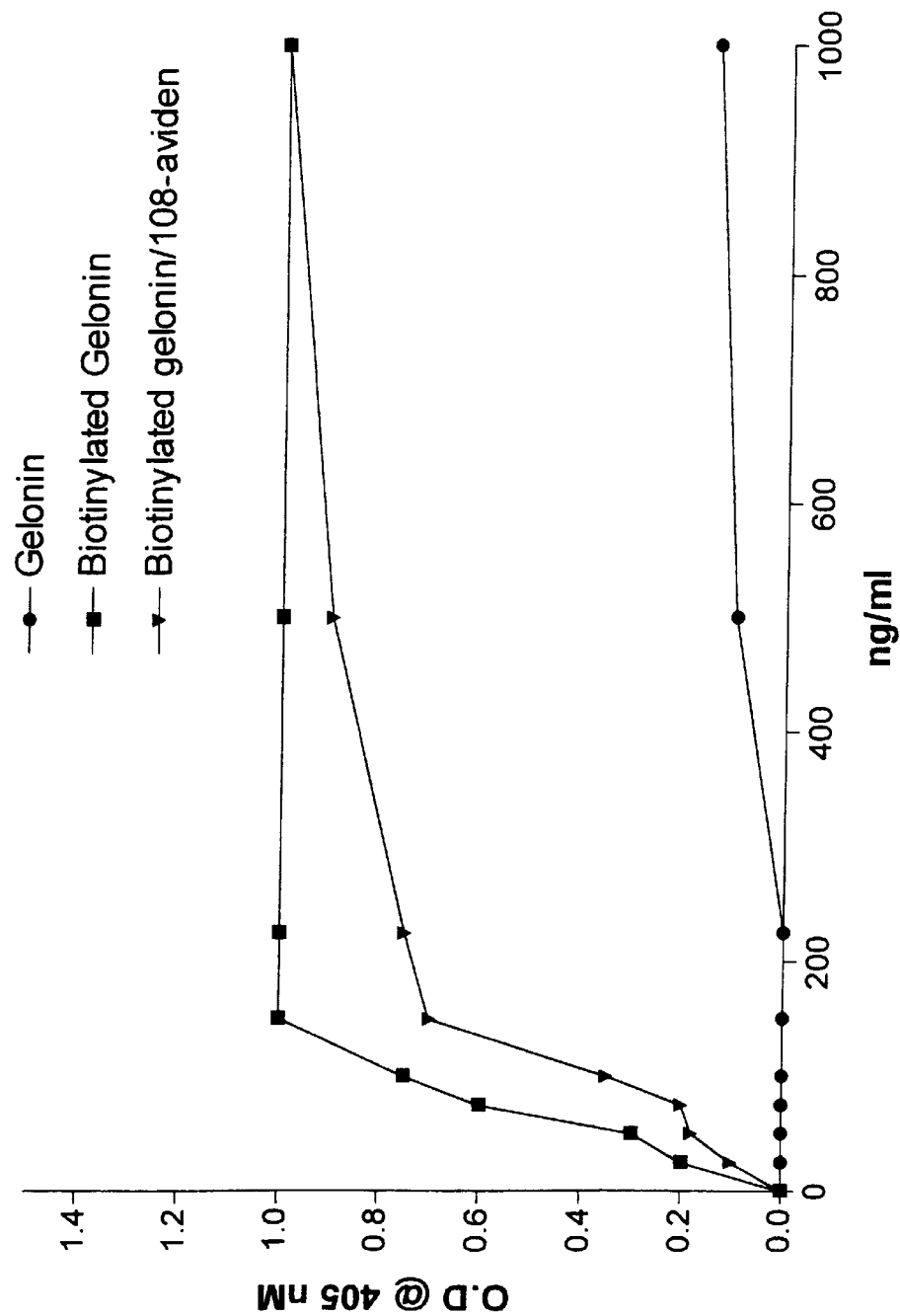
FIG. 8 shows the Elisa binding activity assay for biotinylated gelonin and for A108-avidin biotinylated gelonin conjugate.

The conjugation of A108-avidin with biotinylated gelonin was examined using the same Elisa assay as described above for biotinylated gelonin. As shown in FIG. 8, biotin content could be detected by green color formation when either biotinylated gelonin or biotinylated gelonin:avidin-A108 was tested in the assay. Thus, the conjugate actually contains biotinylated-gelonin.

EXAMPLE 8
Cytotoxicity of A108-avidin/biotinylated gelonin on a431 cells

A431 cells were diluted $3 \times 10^4$ cell/ml in growing media (MEM-minimum essential medium) with nonessential amino acid, 100 mM glutamine and 50 ul gentamicin (Tri-Bio Laboratories) with 5% fetal bovine serum and 5% bovine calf serum. 100 μl of this solution was added to each well of a 96-well microtiter plate (Falcon) and incubated overnight at 37° C. in a 5% $CO_2$ incubator. The next day, a 2 μg/ml solution of A108-gelonin conjugate (Direct conjugate of A108-gelonin using SPDP modified A108 and 2-IT modified gelonin covalently linked to each other through the same chemistry used to prepare A108-avidin) in growing media was prepared, filter-sterilized using a 0.22 micron Acrodisc (Gilman) syringe filter, and serially diluted into ten 15 ml centrifuge tubes (Corning). The A108-avidin:biotinylated gelonin was similarly prepared and 100 μl of each dilution was added in triplicate to the plate. As there was already 100 μl media present in the plate, the final concentration was 1 μg/ml for each conjugate. For a control, the conjugates were prepared in the same way but each with an addition of 100-fold molar excess (100 μg/ml) antibody A108 added to each. The cells were incubated 3 days and then stained with 0.5% crystal violet in 20% methanol and rinsed in distilled water and 150 μl of Sorenson's buffer was added to extract dye from the cells. The plate was then read in the Microplate Autoreader at 540 nm.

Figure 9:
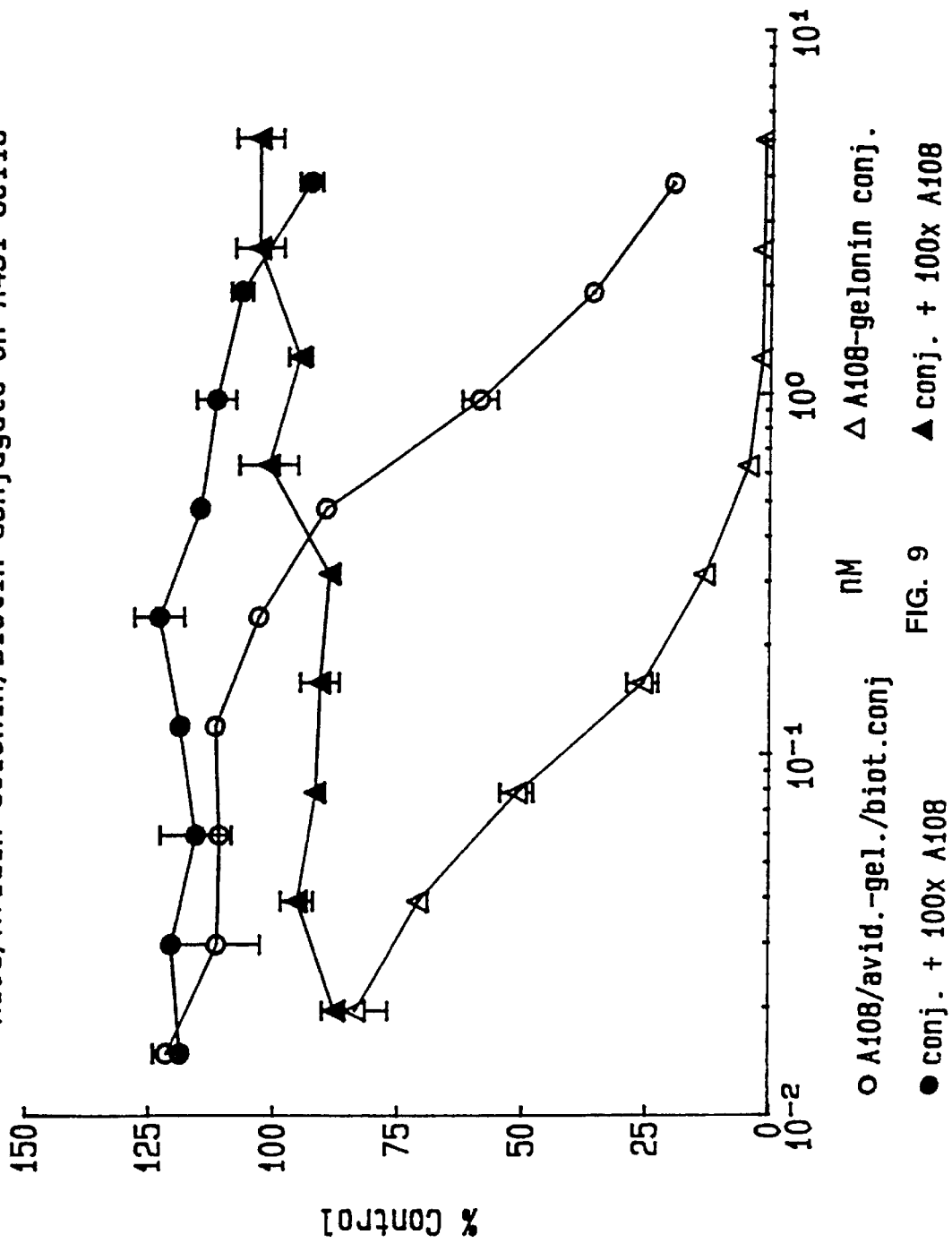
FIG. 9 shows the cytotoxicity of A108-gelonin conjugate compared with the A108-avidin biotinylated gelonin conjugate on A431 cells.

FIG. 9 shows the ability of the conjugate to transfer gelonin to the inside of the cell where it can induce cytotoxicity. The conjugate was incubated with cells that express EGF receptor at their cell surface (A431). Internalization of the conjugate allows the intracellular effects of gelonin, i.e., cytotoxicity to occur. As shown in FIG. 9, when conjugate was incubated with these cells, nanomolar (nM) concentrations ($1 \times 10^{-6}$ molar) killed A431 cells, demonstrating that A108-avidin can allow entry of biotinylated-gelonin into the A431 cell (-open circles). when cells were co-incubated with free A108 antibody in a large excess (when compared to immunoconjugate concentration) the ability of A108-avidin:biotinylated-gelonin to get into the A431 cell was impeded. Free A108 binds all the available EGF receptor on the cell surface, thus inhibiting immunoconjugate from binding EGF receptor and introducing gelonin to the inside of the A431 cell. As shown in FIG. 9, when A108 was present in 100-fold excess compared to the concentration of immunoconjugate (-closed circles), A431 cells were able to survive, demonstrating that the only way immunoconjugate could enter and intoxicate cells was through its ability to bind and be internalized with EGF receptor. The direct covalent conjugate of A108-gelonin was also active in killing A431 by introduction of gelonin into the intracellular compartment of A431 cells (open triangles). Including 100-fold molar excess of free A108 with this direct conjugate also protected cells from intoxication by gelonin, demonstrating that the A108-gelonin was introduced to the intracellular compartment of the cell by its ability to interact and internalize with EGF receptor. Thus, utilization of the avidin:biotin interaction will allow introduction of a molecule into the intracellular compartment of the cell if directed and carried into that compartment with an antibody capable of recognizing an antigen on the cell which is internalized following engagement with the antigen (in this case the EGF receptor).

EXAMPLE 9
Effect of triple helix forming nucleic acid sequences on the expression of EGF receptor protein.

The ability of triple-helix forming oligonucleotide or nucleic acid sequences to suppress the expression of EGF receptor protein in intact cell was demonstrated. A431 cells were incubated for 72 hours with 40 μM EGF receptor gene nucleic acid sequence (#5 EGFr) capable of binding EGF receptor gene promoter region or a non-sense control sequence (which contains the same nucleic acids but in a random sequence.

5 EGFr and control nucleic acid sequences were prepared in media by heating to 950 for 2–5 minutes and filter sterilizing. Growth media was removed from cell culture dishes containing $2 \times 10^5$ A431 cells. #5EGFr diluted in 2 ml media to a final concentration of 40 um was added to 1 dish. Control nucleic acid sequences were diluted in 2 ml media to a final concentration of 40 uM and this solution was added to the second dish of A431 cells. 2 ml of media only was added to the third dish. Incubation was for 72 hours. The cells were harvested by washing each dish three times with ice cold PBS. To solubilize the cell and extract protein, 1 ml RIPA buffer was added and the cells were released with a cell scraper and transferred to a centrifuge tube. Each tube was sonicated with a Kontes cell disrupter and centrifuged in a Sorvall Ultra centrifuge for 1 hour at 4° C. at 100,000×g. After centrifugation, the supernatant was removed and protein content determined with the BCA protein assay (Pierce).

The EGF receptor in these extracts was immunoprecipitated with A108 antibody and the insoluble antibody-binding reagent pansorbin. Supernatant containing 200 μg of protein was incubated for 2 hours at 4° C. with 2.5 μg of antibody A108. 50 μl Pansorbin was added to each sample, vortexed and incubated for 30 minutes at 4° C. The EGF receptor bound to A108-pansorbin was washed to remove other proteins. After centrifugation for 1 minute (4° C.) on a Sorvall microcentrifuge at 12,000 rpm, the supernatant was decanted. The pellet was washed by resuspending 3× with PBS containing 0.1% Triton followed by centrifugation and repelleting by centrifugation after each resuspension. After final washing and centrifugation, the supernatant was poured off.

The EGF receptor present in each immunoprecipitate was detected by incubating it with radioactive ($^{32}$p)labeled-ATP. The pellet was resuspended in 25 μl of 0.4 mM Na vanadate in 20 mM Hepes buffer (pH 7.4). Next, 25 μl of 20 mM Hepes buffer containing $^{32}$P-labeled ATP (10 μCi) and 12 mM $MnCl_2$ was added. Samples were incubated for 5 minutes at room temperature. Since EGF receptor contains an enzyme activity capable of transferring $^{32}$P from ATP to EGF receptor itself, the amount of $^{32}$P transferred to EGF receptor becomes a measure of the quantity of EGF receptor in the immunoprecipitate from each of the lysates. The amount of radioactivity on EGF receptor can be compared by separating the EGF receptor from free $^{32}$P ATP by SDS-PAGE and measuring radioactive EGF receptor by autoradiography of the polyacrylamde gel using commercial x-ray film.

15 μl of 5×-Laemli sample buffer was added to the sample, the sample was heated to 95° C. for 5 minutes and then loaded onto a 7.5% polyacrylamide gel. The proteins were electrophoresed overnight at 14 mA. The gels were removed from the electrophoresis unit and fixed in 40% methanol, 10% acetic acid, 50% ddH$_2$O for 1 hour. The gel was dried on a Bio Rad 583 gel dryer for 2 hours at 80° C.

Figure 10:
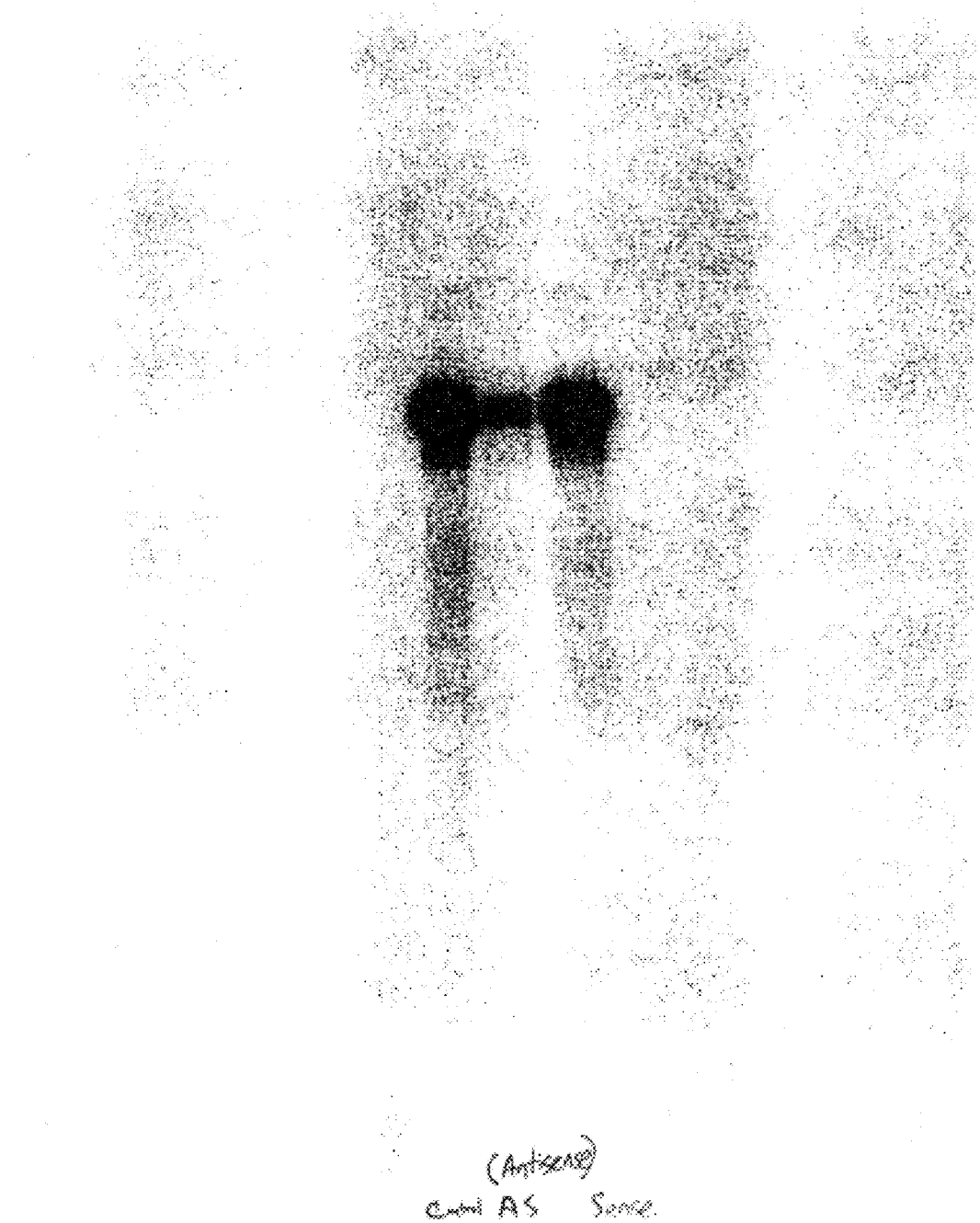
FIG. 10 shows the effect of incubation of cells with nucleic acid sequences directed against the EGF receptor gene promoter sequence (labeled anti-sense EGFr)

As can be seen in FIG. 10, the incubation of cells with nucleic acid sequences directed against the EGF receptor gene promoter sequence (labeled anti-sense EGFr) lowered the level of EGF receptor in A431 cells by five-fold when compared to random nucleic acid sequences (labeled non-sense EGFr) or buffer alone (labeled control). Thus, incubation of cells with high concentrations of triple-helix forming nucleic acid sequences that interact with the promoter region of the EGF receptor gene suppress the expression of EGF receptor in intact A431 cells

EXAMPLE 10

A108:nucleic acid sequences are introduced into A431 cells through an avidin:biotin linkage. To demonstrate that nucleic acid sequences are directed against the EGF receptor gene promoter sequence is incorporated into A431 cells using A108 antibody, the A108-avidin chemically-linked conjugate is made and purified. Nucleic acid sequences are synthesized but with the substitution of a biotinylated-nucleotide for a normal nucleotide at one position in the sequence (preferably at the end or beginning of the sequence). These sequences are incubated with A108-avidin to allow complexes containing A108-avidin:biotin-nucleic acid sequences to form. These hybrid molecules are purified to remove free nucleic acid sequences and the amount of nucleic acid associated with A108-avidin is determined and is incubated with A431 cells. If gene expression-suppressing nucleic acid sequences are incorporated into the correct intracellular region of the A431 cells, it should be biochemically measurable. The specificity of the nucleic acid sequences to interrupt EGF receptor expression is determined by testing immunoconjugates formed between anti-sense EGFr, or non-sense EGFr, with A108-avidin and measuring EGF receptor phosphorylation as described above in Example 9. In addition, the nucleic acid sequences' ability to get into the cell through formation of A108:EGF receptor complexes is tested by including a large molar excess of free A108 in the incubation mixture with A431 cells. The suppressive effects of hybrid molecules composed of antibody:nucleic acid sequences is inhibited in the presence of free A108 and confirms that nucleic acids are introduced into cells by their internalization with antibodies through engagement with an internalizable cell-surface antigen, e.g., the EGF receptor.

EXAMPLE 11

Larger biotinylated-nucleic acids are utilized to determine whether or not their entry into cells is mediated through the A108-avidin mechanism. The concentration of nucleic acid sequences presented to cells through the A108-avidin mechanism which are necessary to alter EGF receptor levels will be compared to normal nucleic acid sequences free in solution. The ability of A108-avidin to direct active nucleic acid sequences to specific antigen expressing cells (e.g., the EGF receptor) is examined using cells which do not express this antigen. The delivery of these nucleic acids to specific cells within animals bearing cells which express this antigen is examined. Suppression of EGF receptor is measured. Both antisense or non-sense nucleic acid sequences complexed with A108-avidin are used (in addition to cells which do not express the specific antigen) as a measure of specificity of this delivery system and its intracellular biochemical specificity.

EXAMPLE 12

A monoclonal anitbody against the breast carcinoma expressed antigen HER2/Neu (e.g., TAb 250) is chemically conjugated to avidin as described in Examples 1–4 for the A108 antibody. Antisense nucleic acid sequences against the antigene c-myc (5'-AACGTTGAGGGGCAT-3') (SEQ D NO. 1) are synthesized with a biotinylated adenine nucleotide replacing the adenosine at the terminal 5' position. The biotinylated adenine nucleic acid sequences are incubated with TAb-250-avidin and antibody-nucleic acid complexes composed of TAb-250:antisense c-myc are purified. These complexes are incubated with breast tumor cells expressing HER2/Neu, e.g., BT-474 cells or cells negative for this antigen, e.g., BT-20 cells. The suppression of c-myc by antisense nucleic acids is measured by western blotting for the c-myc protein from crude cell lysates. C-myc expression will be altered in HER2/Neu positive cells but not in antigen negative cells. Additionally, specificity is implied if a large excess (100-fold) of unmodified TAb-250 is able to inhibit the supressive effects of the antibody-nucleic acid complexes on c-myc in antigen positive cell. The biotinylated nucleic acid sequence is altered by changing the position of the biotinylated-nucleotide within the sequence or by increasing the size of the sequence complementary to and spanning the translation start site or first splice junction on the c-myc mRNA. The modifications are tested to obtain the most specific and sensitive anti-sense sequence deliverable to breast carcinoma cells expressing HER2/Neu antigen which will suppress c-myc expression.

EXAMPLE 13

The monoclonal antibody A108 is conjugated chemically to avidin as described in Examples 1–4. Anti-sense oligonucleotides representing the complementary sequence to the basic fibroblast growth factor (bFGF) mRNA translation start site (5'-GGCTGCCATGGTCCC-3') (SEQ ID NO. 2) are chemically synthesized with a biotinylated guanosine in place of the unmodified nucleotide at the 5'-terminal position. These sequences are incubated with A108-avidin to form antibody:nucleic acid complexes and are purified away from uncomplexed nucleic acid. These complexes are incubated with human glioma cells (SNB-19) which express EGF receptor and are critically dependent on the cells own synthesis of bFGF to promote their own growth. After incubation with this conjugate, SNB cell growth is measured to determine the extent of growth suppression by preventing expression of bFGF in these target cells. As discussed above, excess A108 coincubated with A108:nucleic acid complexes to asses specificity and to confirm the mechanism of entry of antisense sequences through antigen internalization.

EXAMPLE 14

Monoclonal antibody, BR96, which specifically binds Lewis Y antigen on several human carcinomas is chemically conjugated to avidin as described above. Antisense oligonucleotides complementary to the c-Ha-ras 5' flanking mRNA sequence is chemically synthesized 5'-CAGCTGCAACCCAGC-3' ((SEQ ID NO. 3) with a biotinylated cytosine nucleotide in place of unmodified cytosine in the 5' position. BR96-antisense ras oligonucleotides are formed by incubation with T24 bladder carcinoma cells which express Lewis Y antigen and also contain the c-Ha-ras oncogene. After incubation of immune:nucleic acid complexes with T24 cells, the product of the ras oncogene, p21, is monitored by western blotting. Cell growth is also monitored. Neutralization of the effects of ras oncogene by intracellular delivery of antisense molecules through internalization of the Lewis Y antigen is demonstrated.

EXAMPLE 15

A108-avidin chemical conjugate is synthesized as described above and utilized to internalize synthetic double-stranded RNA molecules which are cytotoxic to specific carcinoma cells. A polymer of inosine (PI) is chemically synthesized (40mer) and hybridized to a polycytosine (PC) 39mer with a terminal cytosine derivatized with biotin. This double stranded RNA molecule is incubated with A108-avidin and A108-avidin:biotin-PC:PI complexes are purified and applied to the growth medium of ME-180 cervical carcinoma cells which express EGF receptor and are cytotoxically sensitive to PI:PC (dsRNA). The intracellular delivery of dsRNA though internalization of the EGF receptor is measured by monitoring cell viability following incubation with this construct. Cytotoxicity induced by incubation with this conjugate will show that nucleic acids can be delivered to a specific set of cells with a non-viral vector.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An immunoconjugate preformed and coupled through the avidin-biotin interaction, comprising an internalizable cell binding component having a biotin-binding element conjugated to a biotinylated moiety, wherein said biotinylated moiety is selected from the group consisting of cytotoxic proteins and nucleic acids, wherein said protein is selected from the group consisting of gelonin, ricin, saporin, abrin, diptheria toxin, psuedomonas exotoxin, rayalase, superoxide dismutase, protein tyrosine phosphatase, protein phosphatase (PP-1 or PP-2), protein kinase A and protein kinase C.

2. The immunoconjugate vector of claim 1, wherein said biotin-binding element is selected from the group consisting of avidin, streptavidin or analogues of avidin or streptavidin.

3. The immunoconjugate of claim 1, wherein said cell binding component is a monoclonal antibody.

4. The immunoconjugate vector of claim 3, wherein said monoclonal antibody specifically binds an antigen selected from the group consisting of epidermal growth factor receptor, c-erbB2 antigen, Lewis Y antigen, transferrin receptor, MDR1, MDR3, insulin receptor, CD45, CD33, GP240, GD2, GD3, fibroblast growth factor receptor, and platelet derived growth factor receptor.

5. A method of delivering a cytotoxic moiety to a cell comprising the administration of an immunoconjugate coupled through the avidin-biotin interaction to a human, wherein said immunoconjugate comprises an internalizable cell binding component having a biotin-binding element conjugated to a biotinylated moiety, wherein said biotinylated moiety is selected from the group consisting of cytotoxic proteins and nucleic acids, wherein said protein is selected from the group consisting of gelonin, ricin, saporin, abrin, diptheria toxin, psuedomonas exotoxin, rayalase, superoxide dismutase, protein tyrosine phosphatase, protein phosphatase (PP-1 or PP-2), protein kinase A and protein kinase C.

6. The method of claim 5, wherein said biotin-binding element is selected from the group consisting of avidin, streptavidin and analogues of avidin or streptavidin.

7. The method of claim 5 wherein said cell binding component is a monoclonal antibody.

8. The method of claim 7, wherein said monoclonal antibody specifically binds an antigen selected from the group consisting of epidermal growth factor receptor, c-erbB2 antigen, Lewis Y antigen, transferrin receptor, MDR1, MDR3, insulin receptor, CD45, CD33, GP240, GD2, GD3, fibroblast growth factor receptor, and platelet derived growth factor receptor.

* * * * *

UNITED STATES PATENT AND TRADEMARK OFFICE
CERTIFICATE OF CORRECTION

PATENT NO. : 6,214,974 B1
DATED : April 10, 2001
INVENTOR(S) : Rosenblum et al.

It is certified that error appears in the above-identified patent and that said Letters Patent is hereby corrected as shown below:

Column 6,
Line 66, "is" should read -- are --.
Line 66, "was" should read -- were --.

Column 7,
Line 18, "direct" should read -- direct --.
Line 45, "when" should read -- When --.
Line 60, please delete the space before the period.

Column 8,
Line 13, please delete the word "region" after the word "promoter".
Line 16, please close the parentheses after the word "sequence".
Line 50, please delete the space after "7.4".

Column 9,
Line 33, please delete the period after "anti-sense EGFr".
Line 33, please delete the period after "non-sense EGFr".

Column 10,
Line 3, "SEQ D" should read -- SEQ ID --.

Signed and Sealed this

Ninth Day of July, 2002

*Attest:*

JAMES E. ROGAN
*Attesting Officer*   *Director of the United States Patent and Trademark Office*